United States Patent
Laroche et al.

(10) Patent No.: US 12,251,678 B2
(45) Date of Patent: Mar. 18, 2025

(54) LIQUID PHASE SEPARATION OF SECOND-GENERATION SUGARS BY ADSORPTION ON FAU ZEOLITE HAVING A Si/Al ATOMIC RATIO OF LESS THAN 1.5

(71) Applicant: IFP Energies Nouvelles, Rueil-Malmaison (FR)

(72) Inventors: Catherine Laroche, Rueil-Malmaison (FR); Maria Manko, Rueil-Malmaison (FR); Emmanuelle Bracco, Rueil-Malmaison (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 648 days.

(21) Appl. No.: 17/622,895

(22) PCT Filed: Jun. 11, 2020

(86) PCT No.: PCT/EP2020/066156
§ 371 (c)(1),
(2) Date: Dec. 27, 2021

(87) PCT Pub. No.: WO2020/260028
PCT Pub. Date: Dec. 30, 2020

(65) Prior Publication Data
US 2022/0241749 A1   Aug. 4, 2022

(30) Foreign Application Priority Data
Jun. 28, 2019 (FR) ........................ 1907092

(51) Int. Cl.
| | |
|---|---|
| *B01J 20/18* | (2006.01) |
| *B01D 15/18* | (2006.01) |
| *C02F 1/28* | (2023.01) |
| *B01D 15/20* | (2006.01) |
| *B01D 15/24* | (2006.01) |
| *C13K 13/00* | (2006.01) |

(52) U.S. Cl.
CPC ........... *B01J 20/18* (2013.01); *B01D 15/185* (2013.01); *C02F 1/281* (2013.01); *B01D 15/20* (2013.01); *B01D 15/24* (2013.01); *C13K 13/002* (2013.01); *C13K 13/007* (2013.01)

(58) Field of Classification Search
None
See application file for complete search history.

(56) References Cited

U.S. PATENT DOCUMENTS

| | | | |
|---|---|---|---|
| 4,014,711 A | 3/1977 | Odawara et al. | |
| 4,471,114 A | 9/1984 | Sherman et al. | |
| 4,591,388 A * | 5/1986 | Chao ................ | C13K 13/007 |
| | | | 536/127 |
| RE33,105 E | 10/1989 | Sherman et al. | |
| 6,884,918 B1 | 4/2005 | Plee et al. | |
| 7,452,840 B2 | 11/2008 | Plee et al. | |
| 10,913,695 B2 | 2/2021 | Laroche et al. | |
| 2004/0173533 A1* | 9/2004 | Farone ............. | B01D 15/362 |
| | | | 210/660 |
| 2005/0170947 A1 | 8/2005 | Plee et al. | |
| 2017/0342511 A1 | 11/2017 | Van Den Bergh | |
| 2018/0201555 A1 | 7/2018 | Laroche et al. | |
| 2020/0316558 A1 | 10/2020 | Laroche et al. | |

FOREIGN PATENT DOCUMENTS

| | | | |
|---|---|---|---|
| CN | 103923130 A | 7/2014 | |
| EP | 0115631 A1 | 8/1984 | |
| FR | 2789914 A1 | 8/2000 | |
| GB | 1574915 A * | 9/1980 | ............... C07H 1/06 |
| WO | 00/42225 A1 | 7/2000 | |
| WO | 2016/091588 A1 | 6/2016 | |
| WO | 2017/005907 A1 | 1/2017 | |
| WO | 2019/122650 A1 | 6/2019 | |

OTHER PUBLICATIONS

Chen et al. (Separation and Purification Technology, 2018, 195, 288-294). (Year: 2018).*
Roli et al. (IOP Conf. Series: Materials Science and Engineering, 2017, 162, 012035). (Year: 2017).*
Bi et al. (Analytica Chimica Acta, 2010, 677, 162-168). (Year: 2010).*
Wach et al. (Analytical Methods, 2018, 10, 1817). (Year: 2018).*
International Search Report dated Jul. 28, 2020 issued in corresponding PCT/EP2020/066156 application (4 pages).

* cited by examiner

*Primary Examiner* — Clare M Perrin
(74) *Attorney, Agent, or Firm* — Millen, White, Zelano & Branigan, P.C.; Brion P. Heaney

(57) ABSTRACT

The invention relates to a process for the liquid-phase separation of xylose from a mixture of C5 and C6 sugars comprising at least xylose and glucose, by adsorption of xylose on a zeolitic adsorbent based on FAU-type zeolite crystals having an Si/Al atomic ratio of less than or equal to 1.5 comprising barium, wherein (a) said mixture is brought into contact with said adsorbent, by liquid chromatography, to obtain a glucose-enriched liquid phase and a xylose-enriched adsorbed phase; and (b) on the one hand, said glucose-enriched liquid phase is recovered and said phase adsorbed on said adsorbent is desorbed by means of a desorption solvent in order to recover the xylose on the other hand.

20 Claims, No Drawings

LIQUID PHASE SEPARATION OF SECOND-GENERATION SUGARS BY ADSORPTION ON FAU ZEOLITE HAVING A Si/Al ATOMIC RATIO OF LESS THAN 1.5

TECHNICAL FIELD

The invention relates to the use of adsorbents based on agglomerated crystals of FAU-type zeolite with an Si/Al atomic ratio of less than 1.5, comprising barium for the liquid-phase separation of "second generation" (2G) C5 and C6 sugars, that is to say comprising respectively 5 and 6 carbon atoms, more particularly xylose and glucose.

PRIOR ART

The production of "second generation" sugars from lignocellulosic biomass leads to a mixture of C5 and C6 sugars, essentially consisting of xylose (C5 sugar) and glucose (C6 sugar).

The conversion of these second generation sugars for the production of biobased molecules can be carried out by fermentation or chemically. For chemical conversions, a step of separating the C5 and C6 sugars is necessary. Glucose (C6) can be converted to fructose, sorbitol and gluconic acid. Xylose (C5) can be converted chemically to xylitol, levulinic acid, lactic acid and furfural. Some of these molecules are platform molecules (also called building blocks) which are used in the production of other more complex, high value-added molecules. Levulinic acid is a precursor of polymers and other chemicals such as 2-methyltetrahydrofuran, γ-valerolactone and ethyl levulinate. These synthetic intermediates are used in the synthesis of pharmaceutical compounds or flavors. Lactic acid is a biodegradable polymer precursor used in packaging for skin care and beauty products. Xylitol is a sweetener with an inhibitory nature against the formation of caries, used in the dentistry industry, as an additive in chewing gum and toothpaste.

Today crystalline xylose is produced from second generation (2G) biomass, in particular from sugarcane bagasse, by acid hydrolysis and crystallization. This process remains expensive for several reasons: the hydrolyzate purification steps are lengthy, the physicochemical properties of the impurities are very close to those of xylose and can play an undesirable role as inhibitors, and a portion corresponding to 20% to 30% of the xylose is retained in the mother liquor (S. Silverio da Silva et al., 2012). The complexity of the purification procedures and low product yield result in a high xylose production cost. There is therefore a need to extract the purified xylose from the second generation biomass in order to obtain better profitability, by reusing a large fraction of the lignocellulosic material.

The prior art relating to the separation of xylose and glucose is quite poor. Two separation techniques are cited:
  Membrane separation by nanofiltration: Sjöman et al. tested several nanofiltration membranes, including the NF270 membrane from Dow Liquid Separations, consisting of a semi-aromatic piperazine-based polyamide surface on a polysulfone support. On this type of membrane, the mode of separation is based on the difference in the size of the molecules, as xylose is smaller, it is less retained than glucose. The difference in retention varies depending on the total concentration and on the xylose: glucose ratio in the feedstock and also on the permeation rate.
  Separation by adsorption: technique commonly used for the separation of sugars, and in particular for fructose/glucose separation, according to the simulated moving bed (SMB) process proposed in 1977 by Toray on an adsorbent based on X, Y and L zeolite (Odawara et al., 1979). U.S. Pat. No. 4,340,724 by Neuzil (1982) describes a selection of X and Y zeolites, with a list of exchange cations, for selective adsorption of fructose relative to glucose. The reference adsorbent for the fructose-glucose separation is a calcium-exchanged ion-exchange resin, of styrene-divinylbenzene (DVB) sulfonated copolymer type: this type of resin is offered by UOP for fructose-glucose separation in SMB (Landis et al; 1981). Such resins are now marketed and intended for the enrichment of High Fructose Corn Syrup (fructose-glucose separation) and for the purification of polyols in the food sector, for example the $Ca^2$ exchanged Dowex 99 resin (Dow Water Solutions Brochure, No. 177-01566-0209). No information is available on xylose/glucose separation by selective adsorption on zeolite. In contrast, the $Ca^{2+}$ exchanged Dowex 99 resin is disclosed in patent application US 2004/0173533 for xylose/glucose separation (Farrone, 2004), and shows a slightly greater retention of xylose relative to glucose on this resin. The xylose/glucose selectivity estimated from the pure substance isotherms measured by Lei et al. (J. Chem. Eng. Data, 2010) is however very low (between 1.188 and 1.399).

Despite this low selectivity, the evaluations by Vanneste et al. (Separation and Purification Technology, 2011), show that the separation by chromatographic process on $Ca^{2+}$ exchanged styrene-DVB resin is economically comparable to separation by nanofiltration.

Zeolites, being crystalline materials, find their application in catalysis, adsorption and separation. Among more than two hundred zeolitic structures (http://www.iza-structure.org/databases) it is the FAU-type zeolite which is more used in catalytic industrial processes such as the cracking of heavy petroleum cuts or in the separation of hydrocarbons, more particularly for the production of p-xylene from an aromatic feedstock containing C8 isomers. Faujasite, a FAU-type zeolite, exists in two forms: X form with an Si/Al atomic ratio of between 1 and 1.5 (R. M. Milton, 1959) and Y form with an Si/Al ratio of greater than 1.5 (D. W. Breck, 1964). Y-form faujasite-type zeolites, which find the main application in heterogeneous catalysis, can also be used for the separation of sugars (S. Kulprathipanja, 2017), without further clarification regarding their effectiveness for the separation of glucose and xylose.

Patent application FR 2 903 978 (Bouvier et al., 2008) describes a process for preparing agglomerated zeolitic adsorbents based on small-crystal X zeolite, comprising a step of zeolitization of the binder, and a step of exchange with barium or of exchange with barium and potassium. These adsorbents are used more particularly for the production of very pure para-xylene from a feedstock of aromatic hydrocarbons containing isomers with 8 carbon atoms, but can also be used for the separation of sugars, without further clarification as to the nature of the sugars that these adsorbents are capable of separating. Those skilled in the art are therefore unable to define a priori or theoretically and precisely the adsorption characteristics with respect to xylose and glucose of a particular zeolite.

Surprisingly, it appears that particular agglomerated zeolitic adsorbents have both a good adsorption capacity for sugars and an improved xylose/glucose selectivity, in particular when they are produced from small crystals of FAU zeolite, and can be successfully used in liquid-phase processes for the separation of xylose and glucose contained in "second generation" sugar juices, for example of the simulated countercurrent type.

SUMMARY OF THE INVENTION

The invention relates to a process for the liquid-phase separation of xylose from a mixture of C5 and C6 sugars comprising at least xylose and glucose, by adsorption of xylose on a zeolitic adsorbent based on FAU-type zeolite crystals having an Si/Al atomic ratio of less than or equal to 1.5 comprising barium, wherein:
said mixture is brought into contact with said adsorbent, by liquid chromatography, to obtain a glucose-enriched liquid phase and a xylose-enriched adsorbed phase;
on the one hand, said glucose-enriched liquid phase is recovered and said phase adsorbed on said adsorbent is desorbed by means of a desorption solvent in order to recover the xylose on the other hand.

Said adsorbent may comprise zeolite crystals having a diameter of less than or equal to 2 µm, preferably less than or equal to 1.7 µm.

Preferably, said FAU-type zeolite has an Si/Al atomic ratio such that $(1.00\pm0.05)\leq Si/Al\leq 1.5$, very preferably such that $(1.00\pm0.05)\leq Si/Al\leq 1.3$.

Advantageously, the content of barium oxide BaO in said adsorbent is such that the $Ba^{2+}$ exchange rate is greater than 70%, preferably greater than 90%, and more preferably greater than 95%.

Said adsorbent may comprise potassium and the content of potassium oxide $K_2O$ is advantageously such that the $K^+$ exchange rate is less than 30%, preferably between 0.1% and 5%.

Said adsorbent may comprise strontium and the content of strontium oxide SrO is such that the $Sr^{2+}$ exchange rate is less than 25%, preferably between 0.1% and 5%.

Advantageously, said adsorbent has a total content of oxides of alkali metal or alkaline-earth metal ions other than barium, potassium and sodium, such that the exchange rate of all of said ions relative to all of the alkali metal or alkaline-earth metal ions, is less than 30%, preferably between 0% and 5%.

The separation by adsorption may be carried out in a simulated moving bed: the glucose-enriched liquid phase is removed from contact with the adsorbent thus forming a raffinate stream, and the xylose-enriched phase adsorbed on said adsorbent is desorbed under the action of a desorption solvent, and removed from contact with adsorbent then forming an extract stream.

The desorption solvent can be water.

The separation by adsorption can be carried out in an industrial adsorption unit of simulated countercurrent type with the following operating conditions:
number of beds: 6 to 30
at least 4 operating zones, each located between a feed point and a withdrawal point,
a temperature of from 20° C. to 100° C., preferably from 20° C. to 60° C., very preferably from 20° C. to 40° C.;
pressure of between atmospheric pressure and 0.5 MPa.

Said adsorbent may be in the form of an agglomerate comprising a binder and the number-average diameter of the agglomerates is advantageously from 0.4 to 2 mm, preferably between 0.4 and 0.8 mm.

DESCRIPTION OF THE EMBODIMENTS

Throughout the description, the expressions "between . . . and . . . " and "from . . . to . . . " used in the present description should be understood as including each of the limits mentioned, unless noted otherwise.

The present invention relates to the use of adsorbents based on FAU zeolite having an Si/Al atomic ratio of between 1 and 1.5, comprising barium, and optionally potassium and strontium, for the separation of xylose from a sugar juice containing xylose and glucose, by a simulated countercurrent process.

It has in fact been observed that, surprisingly, a xylose/glucose selectivity of greater than 1.5 could be obtained with adsorbents based on FAU zeolite having an Si/Al atomic ratio of between 1 and 1.5, comprising barium, and optionally potassium and strontium.

The present invention relates to a process for the liquid-phase separation of xylose, preferably of the simulated countercurrent type, from a sugar juice containing xylose and glucose, and using adsorbents based on FAU zeolite having an Si/Al atomic ratio of between 1 and 1.5, comprising barium, and optionally potassium and strontium.

Adsorbents comprising zeolite crystals having a diameter of less than or equal to 2 µm, preferably less than or equal to 1.7 µm, are preferred.

This is because small zeolite crystals generally provide better mass transfer than crystals of the same zeolite with a larger particle size, in particular due to the improved mass transfer. In addition to good selectivity properties with respect to the species to be separated from the reaction mixture, the adsorbent then exhibits good mass transfer properties making it possible to contribute to an efficient separation of the species in the mixture.

The FAU zeolite used is a zeolite having an Si/Al atomic ratio such that $(1.00\pm0.05)\leq Si/Al\leq 1.5$, preferably ranging from $1.00\pm0.05$ to 1.3, limits included, comprising barium, and optionally potassium, or strontium, in order to improve the selectivity toward xylose.

The exchange rate of a given cation is defined as the ratio between the number of moles of oxide $M_{2/n}O$ of the cation $M^{n+}$ considered and the number of moles of all of the alkali metal and alkaline-earth metal oxides.

The contents of elements barium, potassium, strontium, expressed in the form of oxides, are advantageously as follows:
the content of barium oxide BaO is advantageously such that the $Ba^{2+}$ exchange rate is greater than 70%, preferably greater than 90%, and more preferably greater than 95%;
the content of potassium oxide $K_2O$ is advantageously such that the $K^+$ exchange rate is between 0% and 30%, preferably between 0% and 5%;
the content of strontium oxide SrO is advantageously such that the $Sr^{2+}$ exchange rate is between 0% and 25%, preferably between 0% and 5%;
the total content of oxides of alkali metal or alkaline-earth metal ions other than barium, potassium and sodium, is advantageously such that the exchange rate of all of these ions relative to all of the alkali metal or alkaline-earth metal oxides, is less than 30%, preferably between 0% and 5%.

The adsorbent used in the process according to the invention can be obtained by any method known to those skilled in the art, and in particular according to one of the methods described in applications: FR 2 903 978, FR 2 925 366, and FR 2 925 367.

Advantageously, the adsorbent is prepared according to the following steps:
a) mixing the crystals of desired particle size of FAU zeolite having an Si/Al atomic ratio of less than 1.5, in particular such that $(1.00\pm0.05)\leq Si/Al\leq 1.5$, preferably ranging from $1.00\pm0.05$ to 1.3, in the presence of water with at least one binder based on a clay or a mixture of clays, and optionally a source of silica;

b) shaping the mixture obtained in a) to produce agglomerates, then drying, optionally followed by a screening and/or cycloning step;

c) calcining the agglomerates obtained in b) at a temperature preferentially ranging from 500° C. to 600° C.;

d) optionally zeolitizing the binder by bringing the calcined agglomerates resulting from step c) into contact with an alkali metal basic aqueous solution, followed by washing;

e) ion exchange of the zeolitic agglomerates obtained in c) or in d) with barium ions, followed by washing and drying of the product thus treated;

f) the optional exchange with potassium or strontium may be carried out before and/or after the exchange with barium (step e), followed by washing and drying of the product thus treated.

The shaping step b) makes it possible to obtain zeolitic agglomerates having sufficient mechanical strength for the use thereof in a process for separating a liquid mixture in a simulated moving bed. However, the presence of binder reduces the proportion of active material in the adsorption sense, said active material being the FAU zeolite having an Si/Al atomic ratio such that $(1.00\pm0.05)\leq Si/Al\leq 1.5$.

The optional step d) of zeolitizing the binder thus makes it possible to convert all or part of the binder into active material in the adsorption sense (FAU zeolite having an Si/Al atomic ratio such that $(1.00\pm0.05)\leq Si/Al\leq 1.5$) in order to obtain binder-free agglomerates, i.e. no longer comprising a non-zeolitic phase (in an amount typically of less than 2%), or agglomerates with a low binder content, i.e. comprising little (an amount typically of between 2% and 5%) of non-zeolitic phase (generally non-zeolitized residual binder or any other amorphous phase after zeolitization) in the final agglomerate, while maintaining the mechanical strength.

The agglomerates resulting from step c/ or d/, whether they are in the form of beads or extrudates, generally have a number-average diameter ranging from 0.4 to 2 mm, and in particular between 0.4 and 0.8 mm.

The present invention more particularly relates to a process for the liquid-phase separation of xylose from a sugar juice containing xylose and glucose, taking place by liquid adsorption chromatography, advantageously in a simulated moving bed, i.e. simulated countercurrent or simulated cocurrent moving bed, and more particularly simulated countercurrent moving bed.

The desorption solvent is preferably water.

In a liquid-phase adsorption separation process, the adsorbent solid is brought into contact with the liquid feed stream (feedstock) composed of a sugar juice containing xylose and glucose. By using a zeolitic adsorbent based on a zeolite of faujasite structure having an Si/Al atomic ratio such that $(1.00\pm0.05)\leq Si/Al\leq 1.5$ and comprising barium, and optionally potassium and strontium, the xylose is then adsorbed in the micropores of the zeolite preferentially with respect to the glucose. The phase adsorbed in the micropores of the zeolite is then enriched in xylose relative to the initial mixture constituting the feed stream. Conversely, the liquid phase is enriched in glucose relative to the initial mixture constituting the feed stream.

When the process takes place in a simulated moving bed, the glucose-enriched liquid phase is then removed from contact with the adsorbent thus forming a raffinate stream, and the xylose-enriched adsorbed phase is desorbed under the action of a desorption stream (or desorption solvent), and removed from contact with the adsorbent then forming an extract stream.

In general, the operation of a simulated moving bed column can be described as follows:

A column comprises at least four zones, each of these zones being made up of a certain number of successive beds, and each zone being defined by its position between a feed point and a withdrawal point. Typically, a simulated moving bed unit for the separation of sugars is fed with at least one feedstock F to be fractionated (sugar juice) and one desorbent D, sometimes referred to as a desorption solvent or eluent (generally water), and at least one raffinate R containing the least selectively adsorbed feedstock products and desorbent and an extract E containing the most adsorbed feedstock product and desorbent are withdrawn from said unit.

Conventionally, 4 different chromatographic zones are defined in a column operating in simulated countercurrent mode.

Zone 1: zone for desorption of the most adsorbed feedstock product, between the injection of the desorbent D and the withdrawal of the extract E.

Zone 2: zone for desorption of the least selectively adsorbed feedstock products, between the withdrawal of the extract E and the injection of the feedstock to be fractionated F.

Zone 3: zone for adsorption of the most adsorbed feedstock product, between the injection of the feedstock and the withdrawal of the raffinate R.

Zone 4: zone located between the withdrawal of the raffinate R and the injection of the desorbent D.

The operating conditions of an industrial adsorption unit of simulated countercurrent type are advantageously the following:

number of beds: 6 to 30, at least 4 operating zones, each located between a feed point and a withdrawal point, temperature of from 20° C. to 100° C., preferably from 20° C. to 60° C., very preferably from 20° C. to 40° C., pressure of between atmospheric pressure and 0.5 MPa.

One of the techniques of choice for characterizing the adsorption of molecules in the liquid phase on a porous solid is to carry out a breakthrough. In his book "Principles of Adsorption and Adsorption Processes", Ruthven defines the technique of breakthrough curves as the study of the injection of a range of adsorbable constituents.

BIBLIOGRAPHY

S. Silverio da Silva, A. K. Chandel, *Fermentative Production, Application and Commercialization*, Springer-Verlag Berlin, Heidelberg, 2012

E. Sjoman, M. Manttari, M. Nystrom, H. Koivviko, H. Heikkila, *Separation of xylose grom glucose by nanofiltration from concentrated monosaccharide solutions*, Journal of Membrane Science, vol. 292, (1-2), p. 106-115, 2007

Odawara et al., U.S. Pat. No. 4,157,267, 1979

Neuzil, U.S. Pat. No. 4,340,724, 1982

Landis, Broughton, Fickel, U.S. Pat. No. 4,293,346, 1981

Brochure Dow Water Solutions, Dowex™ Monosphere™, *Chromatographic Separation of Fructose and Glucose with Dowex Monosphere Ion Exchange Resin*, Technical Manual, No. 177-01566-0209

Farrone, US 2004173533, 2004

H. Lei, Z. Bao, H. Xing, Y. Yang, Q. Ren, M. Zhao, H. Huang, *Adsorption Behavior of Glucose, Xylose and Arabinose on Five Different Cation Exchange Resins*, J. Chem. Eng. Data, vol. 55, (2), p. 735-738, 2010

J. Vanneste, S. de Ron, S. Vandecruys, S. A. Soare, S. Darvishmanesh, B. van der Bruggen, *Techno-economic evaluation of membrane cascades relative to stimulated moving bed chromatography for the purification of mono- and oligosaccharides*, Separation and Purification Technology 80, 600-609, 2011 http://www.iza-structure.org/databases

R. M. Milton, U.S. Pat. No. 2,882,244, 1959

D. W. Breck, U.S. Pat. No. 3,130,007, 1964

S. Kulprathipanja, *Zeolites in Industrial Separation and Catalysis*; Wiley-VCH, Verlag, 2010

L. Bouvier, S. Kieger, C. Laroche, P. Leflaive, D. Plee, *Adsorbants zeolitiques agglomeres, leur procede de preparation et leurs utilisations* [Agglomerated zeolitic adsorbents, process for the preparation thereof and uses of same], FR 2 903 978, 2008.

L. Bouvier, S. Kieger, C. Laroche, P. Leflaive, T. Frising, *Adsorbants zeolitiques agglomeres, leur procédé de preparation et leurs utilisations* [Agglomerated zeolitic adsorbents, process for the preparation thereof and uses of same], FR 2 925 366, 2007.

L. Bouvier, S. Kieger, C. Laroche, P. Leflaive, T. Frising, *Adsorbants zeolitiques agglomeres, leur procédé de préparation et leurs utilisations* [Agglomerated zeolitic adsorbents, process for the preparation thereof and uses of same], FR 2 925 367, 2007.

D. M. Ruthven, *Principles of adsorption & adsorption processes*, John Wiley & Sons, 1984

EXAMPLES

Several types of adsorbents are prepared: zeolitic adsorbents based on X zeolite (A to G), zeolitic adsorbents based on Y zeolite (H, I), ion-exchange resins (J, K).

The characteristics of the adsorbents are as follows:

A: Adsorbent based on X zeolite in sodium form having an Si/Al atomic ratio equal to 1.23, used in the form of a 0.6 mm diameter bead.

B: Adsorbent based on X zeolite having an Si/Al atomic ratio equal to 1.23 exchanged with calcium ions such that the calcium exchange rate is 95%, used in the form of a 0.6 mm diameter bead.

C: Adsorbent based on LSX zeolite having an Si/Al atomic ratio equal to 1.02 exchanged with barium ions such that the barium exchange rate is 98%, used in the form of a 0.6 mm diameter bead.

D: Adsorbent based on X zeolite having an Si/Al atomic ratio equal to 1.23 exchanged with barium ions such that the barium exchange rate is 99%, used in the form of a 0.6 mm diameter bead.

E: Adsorbent based on X zeolite having an Si/Al atomic ratio equal to 1.23 exchanged both with barium and potassium such that the barium exchange rate is 93% and the potassium exchange rate is 5%, used in the form of a 0.6 mm diameter bead.

F: Adsorbent based on X zeolite having an Si/Al atomic ratio equal to 1.23 exchanged both with barium and strontium such that the barium exchange rate is 79% and the strontium exchange rate is 21%, used in the form of a 0.6 mm diameter bead.

G: Adsorbent based on X zeolite having an Si/Al atomic ratio equal to 1.23 exchanged both with barium and potassium such that the barium exchange rate is 74% and the potassium exchange rate is 26%, used in the form of a 0.6 mm diameter bead.

H: Adsorbent based on Y zeolite having an Si/Al atomic ratio equal to 2.74 exchanged with barium such that the barium exchange rate is 65%, the other cations present being sodium, used in the form of a 0.6 mm diameter bead.

I: Adsorbent based on Y zeolite having an Si/Al atomic ratio equal to 2.74 exchanged both with barium and potassium such that the exchange rate for each of the cations is around 50%, used in the form of a 0.6 mm diameter bead.

J: $Ca^{2+}$ exchanged Dowex® 99 resin

K: Dowex® 99 resin initially with calcium, exchanged with barium

A breakthrough test (frontal chromatography) is performed with the adsorbents A to K to evaluate their efficiency.

The procedure for obtaining the breakthrough curves is as follows:

Filling a column of about 20 cm³ with the adsorbent and insertion in the test bench.

Filling with the solvent (water) at ambient temperature.

Gradual increase to the adsorption temperature (30° C.) under a stream of solvent with a flow rate of 0.5 cm³/min.

Solvent/feedstock changeover to inject the feedstock with a flow rate of 0.5 cm³/min.

Online Raman analysis of the effluent and optional collection for offline analysis by other techniques for analyzing sugars (HPLC, etc.).

The injection of the feedstock is maintained for a sufficient time for the composition of the effluent to correspond to the composition of the feedstock.

The pressure is sufficient for the feedstock to remain in liquid phase at the adsorption temperature (30° C.), i.e. 0.12 MPa.

The composition of the feedstock used for the tests is as follows:

xylose: 0.145 g/g glucose: 0.145 g/g

The selectivity of the xylose (X) relative to the glucose (G) is calculated from the adsorbed mass quantities $q_X$ and $q_G$ of the two compounds (the latter being determined by material balance from the analysis of the breakthrough effluent) and of the composition of the feedstock (feedstock in which the mass fraction of the compounds is $y_X$ and $y_G$):

$$\cdot a_{X/G} = \frac{q_X y_G}{q_G y_X}.$$

The breakthrough results are given in Table 1 below:

TABLE 1

| Adsorbent | | Qads Xylose (g/g) | Qads Glucose (g/g) | Xylose/Glucose selectivity |
|---|---|---|---|---|
| Comparative | A | 0.038 | 0.049 | 0.8 |
| Comparative | B | 0.016 | 0.024 | 0.7 |
| According to the invention | C | 0.042 | 0.018 | 2.1 |
| According to the invention | D | 0.063 | 0.021 | 2.9 |
| According to the invention | E | 0.063 | 0.030 | 2.1 |
| According to | F | 0.051 | 0.032 | 1.6 |

TABLE 1-continued

| Adsorbent | | Qads Xylose (g/g) | Qads Glucose (g/g) | Xylose/Glucose selectivity |
|---|---|---|---|---|
| the invention According to the invention | G | 0.063 | 0.032 | 2.0 |
| Comparative | H | 0.031 | 0.068 | 0.5 |
| Comparative | I | 0.023 | 0.033 | 0.7 |
| Comparative | J | 0.034 | 0.032 | 1.1 |
| Comparative | K | 0.040 | 0.038 | 1 |

The example shows that the zeolitic adsorbents in accordance with the invention have improved properties of selectivity of xylose relative to glucose compared to the adsorbents or resins known from the prior art.

The invention claimed is:

1. A process for the liquid-phase separation of xylose from a mixture of C5 and C6 sugars comprising at least xylose and glucose, said process comprising:
   adsorbing xylose on a zeolitic adsorbent based on FAU-type zeolite crystals having an Si/Al atomic ratio of less than or equal to 1.5 comprising barium;
   by bringing said mixture into contact with said adsorbent, by liquid chromatography, to obtain a glucose-enriched liquid phase and a xylose-enriched adsorbed phase; and
   recovering said glucose-enriched liquid phase and desorbing said adsorbed phase from said adsorbent by means of a desorption solvent in order to recover xylose.

2. The process as claimed in claim 1, wherein said adsorbent comprises zeolite crystals having a diameter of less than or equal to 2 μm.

3. The process as claimed in claim 1, wherein said FAU-type zeolite has an Si/Al atomic ratio such that $(1.00\pm0.05)\leq Si/Al\leq 1.5$.

4. The process as claimed in claim 1, wherein the content of barium oxide BaO in said adsorbent is such that the $Ba^{2+}$ exchange rate is greater than 70%.

5. The process as claimed in claim 1, wherein said adsorbent comprises potassium and the content of potassium oxide $K_2O$ is such that the $K^+$ exchange rate is less than 30%.

6. The process as claimed in claim 1, wherein said adsorbent comprises strontium and the content of strontium oxide SrO is such that the $Sr^{2+}$ exchange rate is less than 25%.

7. The process as claimed in claim 1, wherein said adsorbent has a total content of oxides of alkali metal or alkaline-earth metal ions other than barium, potassium and sodium, such that the exchange rate of all of said ions relative to all of the alkali metal or alkaline-earth metal ions, is less than 30%.

8. The process as claimed in claim 1, wherein the separation by adsorption is carried out in a simulated moving bed: the glucose-enriched liquid phase is removed from contact with the adsorbent thus forming a raffinate stream, and the xylose-enriched phase adsorbed on said adsorbent is desorbed under the action of a desorption solvent, and removed from contact with the adsorbent to form an extract stream.

9. The process as claimed in claim 8, wherein the separation by adsorption is carried out in an industrial adsorption unit of simulated countercurrent type with the following operating conditions:
   number of beds: 6 to 30
   at least 4 operating zones, each located between a feed point and a withdrawal point,
   a temperature of from 20° C. to 100° C.;
   pressure of between atmospheric pressure and 0.5 MPa.

10. The process as claimed in claim 9, wherein the operating temperature is from 20° C. to 60° C.

11. The process as claimed in claim 9, wherein the operating temperature is from 20° C. to 40° C.

12. The process as claimed in claim 1, wherein the desorption solvent is water.

13. The process as claimed in claim 1, wherein said adsorbent is in the form of agglomerates comprising a binder and the number-average diameter of the agglomerates is from 0.4 to 2 mm.

14. The process as claimed in claim 1, wherein said adsorbent comprises zeolite crystals having a diameter of less than or equal to 1.7 μm.

15. The process as claimed in claim 1, wherein said FAU-type zeolite has an Si/Al atomic ratio such that $(1.00\pm0.05)\leq Si/Al\leq 1.3$.

16. The process as claimed in claim 1, wherein the content of barium oxide BaO in said adsorbent is such that the $Ba^{2+}$ exchange rate is greater than 90%.

17. The process as claimed in claim 1, wherein said adsorbent comprises potassium and the content of potassium oxide $K_2O$ is such that the $K^+$ exchange rate is between 0.1% and 5%.

18. The process as claimed in claim 1, wherein said adsorbent comprises strontium and the content of strontium oxide SrO is such that the $Sr^{2+}$ exchange rate is between 0.1% and 5%.

19. The process as claimed in claim 1, wherein said adsorbent has a total content of oxides of alkali metal or alkaline-earth metal ions other than barium, potassium and sodium, such that the exchange rate of all of said ions relative to all of the alkali metal or alkaline-earth metal ions, is between 0% and 5%.

20. The process as claimed in claim 1, wherein said adsorbent is in the form of an agglomerate comprising a binder and the number-average diameter of the agglomerates is between 0.4 and 0.8 mm.

* * * * *